(12) United States Patent
Niwayama

(10) Patent No.: US 12,422,246 B2
(45) Date of Patent: Sep. 23, 2025

(54) MEASUREMENT SENSITIVITY CALCULATION METHOD, MEASUREMENT SENSITIVITY CALCULATION DEVICE, RECORDING MEDIUM STORING MEASUREMENT SENSITIVITY CALCULATION PROGRAM, AND OPTICAL MEASUREMENT DEVICE

(71) Applicant: National University Corporation Shizuoka University, Shizuoka (JP)

(72) Inventor: Masatsugu Niwayama, Hamamatsu (JP)

(73) Assignee: NATIONAL UNIVERSITY CORPORATION SHIZUOKA UNIVERSITY, Shizuoka (JP)

( * ) Notice: Subject to any disclaimer, the term of this patent is extended or adjusted under 35 U.S.C. 154(b) by 372 days.

(21) Appl. No.: 18/246,384

(22) PCT Filed: Sep. 22, 2021

(86) PCT No.: PCT/JP2021/034881
§ 371 (c)(1),
(2) Date: Mar. 23, 2023

(87) PCT Pub. No.: WO2022/065390
PCT Pub. Date: Mar. 31, 2022

(65) Prior Publication Data
US 2023/0366669 A1    Nov. 16, 2023

(30) Foreign Application Priority Data
Sep. 25, 2020    (JP) ................. 2020-161401

(51) Int. Cl.
*G01B 9/02055* (2022.01)
*G01N 21/359* (2014.01)

(52) U.S. Cl.
CPC ....... *G01B 9/02069* (2013.01); *G01N 21/359* (2013.01)

(58) Field of Classification Search
CPC ................ A61B 3/102; G01B 9/02028; G01B 9/02091; G01B 9/02069; G01N 21/359
See application file for complete search history.

(56) References Cited

U.S. PATENT DOCUMENTS

| 5,902,235 A | 5/1999 | Lewis et al. |
| 8,369,914 B2 | 2/2013 | Niwayama |

(Continued)

FOREIGN PATENT DOCUMENTS

| EP | 0 942 260 A1 | 9/1999 |
| JP | H8-322821 A | 12/1996 |

(Continued)

OTHER PUBLICATIONS

International Search Report and Written Opinion for Application No. PCT/JP2021/034881, dated Dec. 14, 2021.

(Continued)

*Primary Examiner* — Gerald Johnson
(74) *Attorney, Agent, or Firm* — MARSHALL, GERSTEIN & BORUN LLP

(57) ABSTRACT

In a measurement target model representing a measurement target, this measurement sensitivity calculation device uses, as measurement sensitivity, an optical path length difference between a first optical path length indicating the length of an optical path through which light emitted from a light emitter to the measurement target travels before being received by a first light receiver spaced apart by a first distance from the light emitter and a second optical path length indicating the length of an optical path through which light emitted from the light emitter travels before being received by a second light receiver spaced apart by a second distance from the (Continued)

light emitter, calculates the measurement sensitivity for each depth of the measurement target, and outputs the measurement sensitivity calculated for each depth of the measurement target.

9 Claims, 24 Drawing Sheets

(56) References Cited

U.S. PATENT DOCUMENTS

| | | | |
|---|---|---|---|
| 9,433,352 | B2 | 9/2016 | Niwayama et al. |
| 2012/0200859 | A1* | 8/2012 | Breitenstein ....... G01B 9/02091 356/479 |
| 2014/0039284 | A1 | 2/2014 | Niwayama et al. |
| 2015/0223694 | A1 | 8/2015 | Funane et al. |

FOREIGN PATENT DOCUMENTS

| | | |
|---|---|---|
| JP | H11-239573 A | 9/1999 |
| JP | 2017-161424 A | 9/2017 |
| JP | 2019-158523 A | 9/2019 |
| WO | WO-98/23916 A1 | 6/1998 |
| WO | WO-2007/139192 A1 | 12/2007 |
| WO | WO-2012/115210 A1 | 8/2012 |
| WO | WO-2014/034285 A1 | 3/2014 |

OTHER PUBLICATIONS

Niwayama, "Voxel-Based Measurement Sensitivity of Spatially Resolved Near-Infrared Spectroscopy in Layered Tissues," Journal of Biomedical Optics 23(3):030503-1-030503-4 (2018).
English translations of Article 34 claim amendments and response to Written Opinion.

* cited by examiner

[FIG.8]
FIG.8
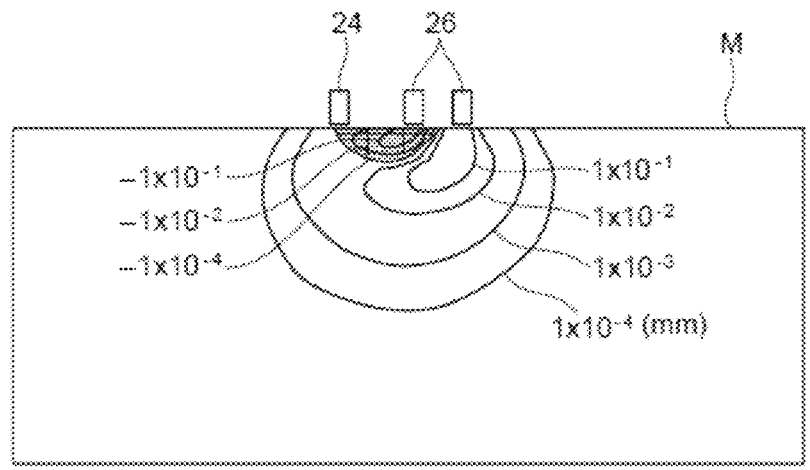
 REGION OF NEGATIVE MEASUREMENT SENSITIVITY

MEASUREMENT SENSITIVITY CALCULATION METHOD, MEASUREMENT SENSITIVITY CALCULATION DEVICE, RECORDING MEDIUM STORING MEASUREMENT SENSITIVITY CALCULATION PROGRAM, AND OPTICAL MEASUREMENT DEVICE

TECHNICAL FIELD

The present disclosure relates to a measurement sensitivity calculation method, a measurement sensitivity calculation device, a measurement sensitivity calculation program, and an optical measurement device.

BACKGROUND ART

Mainly a continuous wave technique (a technique that measures the amount of change in oxygen concentration by a pair of one light source and one light receiver), a spatial resolution technique (a technique that determines the absolute value of the oxygen concentration from the difference in the spatial light amounts at a pair of one light source and two light receivers), a temporal resolution technique, and a phase modulation technique have been put into practice in hemodynamic measurement using conventional near-infrared spectroscopy (NIRS).

Measurement methods using the continuous wave technique are disclosed in Patent Documents 1, 2 for example. Further, a measurement method using the spatial resolution technique is disclosed in Non-Patent Document 1.

With regard to the problem of the measurement depth at the object of measurement, which is about what depth from the body surface measurement can be carried out, it is generally known that a distance that is approximately half of the distance between the light transmitter and the light receiver is the measurement depth, based on depths of a range called the banana shape that expresses the range of measurement in the continuous wave technique.

Patent Document 1: International Publication No. 2014/34285
Patent Document 2: U.S. Pat. No. 5,902,235
Non-Patent Document 1: Masatsugu Niwayama, "Voxel-based measurement sensitivity of spatially resolved near-infrared spectroscopy in layered tissues", Biomedical Optics_2018.3:

SUMMARY OF INVENTION

Technical Problem

However, if the measurement depth in the spatial resolution technique is made to be approximately half of the distance between the light transmitter and the light receiver in the same way as in NIRS in accordance with the continuous wave technique, there are the problems that the error becomes large, and further, the true measurement sensitivity is not obtained in principle.

The present disclosure was made in consideration of the above-described circumstances, and an object thereof is to provide a measurement sensitivity calculation method, a measurement sensitivity calculation device, a measurement sensitivity calculation program, and an optical measurement device that can accurately calculate the measurement sensitivity per depth of an object of measurement.

Solution to Problem

In order to achieve the above-described object, in a measurement sensitivity calculation method relating to a first aspect, a computer executes processings comprising: a step of, in an object of measurement model that expresses an object of measurement, calculating measurement sensitivity per depth of the object of measurement by using, as the measurement sensitivity, an optical path length difference between a first optical path length expressing a length of a first optical path that is up to where light, which is emitted from a light emitter onto the object of measurement, is received at a first light receiver that is apart from the light emitter by a first distance, and a second optical path length expressing a length of a second optical path that is up to where light, which is emitted from the light emitter, is received at a second light receiver that is apart from the light emitter by a second distance; and a step of outputting the calculated measurement sensitivity per depth of the object of measurement.

In the measurement sensitivity calculation method relating to the first aspect, the step of calculating may select a plurality of groups of two light receivers that are combinations in which at least one of the first distance and the second distance is different, and calculate the measurement sensitivity per depth of the measurement object for the plurality of groups of light receivers that are selected.

In the measurement sensitivity calculation method relating to the first aspect, the step of outputting may output the first distance and the second distance of a group of light receivers at which a depth of the object of measurement is included in a range of depths corresponding to a measurement sensitivity that is greater than or equal to a predetermined threshold value, among the plurality of groups of light receivers.

In the measurement sensitivity calculation method relating to the first aspect, the object of measurement model is a model expressing the object of measurement by a plurality of voxels, and the step of calculating may calculate the measurement sensitivity per depth of the object of measurement by, for each of the plurality of voxels, calculating the first optical path length and the second optical path length and calculating the measurement sensitivity, and integrating the measurement sensitivities calculated for the respective voxels per depth of the object of measurement.

A measurement sensitivity calculation device relating to a second aspect comprises: a calculating section that, in an object of measurement model that expresses an object of measurement, calculates measurement sensitivity per depth of the object of measurement by using, as the measurement sensitivity, an optical path length difference between a first optical path length expressing a length of an optical path that is up to where light, which is emitted from a light emitter onto the object of measurement, is received at a first light receiver that is apart from the light emitter by a first distance, and a second optical path length expressing a length of an optical path that is up to where light, which is emitted from the light emitter, is received at a second light receiver that is apart from the light emitter by a second distance; and an outputting section that outputs the calculated measurement sensitivity per depth of the object of measurement.

A measurement sensitivity calculation program relating to a third aspect causes a computer to execute processings comprising: a step of, in an object of measurement model that expresses an object of measurement, calculating measurement sensitivity per depth of the object of measurement by using, as the measurement sensitivity, an optical path length difference between a first optical path length expressing a length of a first optical path that is up to where light, which is emitted from a light emitter onto the object of measurement, is received at a first light receiver that is apart from the light emitter by a first distance, and a second optical path length expressing a length of a second optical path that is up to where light, which is emitted from the light emitter, is received at a second light receiver that is apart from the light emitter by a second distance; and a step of outputting the calculated measurement sensitivity per depth of the object of measurement.

An optical measurement device relating to a fourth aspect comprises: a light emitter emitting light onto an object of measurement; three or more light receivers selected from among plural groups of light receivers selected by the measurement sensitivity calculation method relating to the first aspect; a selecting section selecting two light receivers from the three or more light receivers; and a computing section that calculates absorption degrees of lights on the basis of light intensities of lights received by the two light receivers.

The optical measurement device relating to the fourth aspect may further comprise: measuring sections measuring times of flight in a positional relationship that is the same as a positional relationship between the light emitter and two, predetermined light receivers among the three or more light receivers; and a specifying section that causes lights of a plurality of wavelengths to be emitted from the light emitter, and specifies the object of measurement corresponding to an absorption coefficient and a scattering coefficient that are calculated on the basis of the times of flight and a spatial slope calculated on the basis of intensities of lights received at the two light receivers, wherein the selecting section may select, from among the three or more light receivers, two light receivers that correspond to the object of measurement specified by the specifying section.

An optical measurement device relating to a fifth aspect comprises: a light emitter emitting light onto an object of measurement; three or more light receivers whose distances from the light emitter are different; a selecting section selecting two light receivers that are selected from the three or more light receivers; and a computing section that calculates absorption degrees of lights on the basis of light intensities of lights received by the two light receivers.

In the optical measurement device relating to the fifth aspect, in an object of measurement model that expresses an object of measurement, and by using, as measurement sensitivity, an optical path length difference between a first optical path length expressing a length of a first optical path that is up to where light, which is emitted from the light emitter onto the object of measurement, is received at a first light receiver that is apart from the light emitter by a first distance, and a second optical path length expressing a length of a second optical path that is up to where light, which is emitted from the light emitter, is received at a second light receiver that is apart from the light emitter by a second distance, the selecting section may select a plurality of groups of two light receivers that are combinations in which at least one of the first distance and the second distance is different, and may select two light receivers corresponding to the object of measurement on the basis of calculation results of calculating the measurement sensitivity per depth of the object of measurement for the plurality of groups of light receivers that were selected.

In the optical measurement device relating to the fifth aspect, in a case in which the object of measurement is skin tissue, and a depth of the object of measurement is greater than or equal to 1 mm and less than or equal to 3 mm, the selecting section may select the second light receiver at which the second distance is less than or equal to 14 mm.

In the optical measurement device relating to the fifth aspect, in a case in which the object of measurement is skin tissue, the selecting section may select the first light receiver and the second light receiver that correspond to the first distance and the second distance that are nearest to the first distance and the second distance that satisfy conditions that the first distance is ½ of the second distance and a depth of the skin tissue is ⅕ of the second distance.

In the optical measurement device relating to the fifth aspect, the selecting section may select the first light receiver and the second light receiver on the basis of a relationship of correspondence among a depth of the object of measurement, the first distance and the second distance, which relationship of correspondence is derived on the basis of calculation results of calculating the measurement sensitivity per depth of the object of measurement.

An optical measurement device relating to a sixth aspect comprises: a light emitter emitting light onto an object of measurement; two or more light receivers whose distances from the light emitter are different; and a measuring section adjacent to at least one light receiver among the two or more light receivers, and measuring a time of flight of the light.

The optical measurement device relating to the sixth aspect may be structured so as to comprise a calculating section that causes lights of a plurality of wavelengths to be emitted from the light emitter, and calculates information relating to at least one of an absorption coefficient and a scattering coefficient on the basis of the times of flight and a spatial slope that is calculated on the basis of intensities of lights received at the two or more light receivers.

The optical measurement device relating to the sixth aspect may be structured so as to comprise: a specifying section specifying the object of measurement corresponding to at least one of the absorption coefficient and the scattering coefficient calculated by the calculating section; and a selecting section selecting two or more light receivers that correspond to the object of measurement specified by the specifying section.

Advantageous Effects of Invention

In accordance with the present disclosure, there is the effect that measurement sensitivity can be accurately calculated for each depth of the object of measurement.

BRIEF DESCRIPTION OF DRAWINGS

FIG. 8 is a drawing illustrating an example of measurement sensitivity distribution.

DESCRIPTION OF EMBODIMENTS

Embodiments of the present disclosure are described in detail hereinafter with reference to the drawings.

First Embodiment

Figure 1:
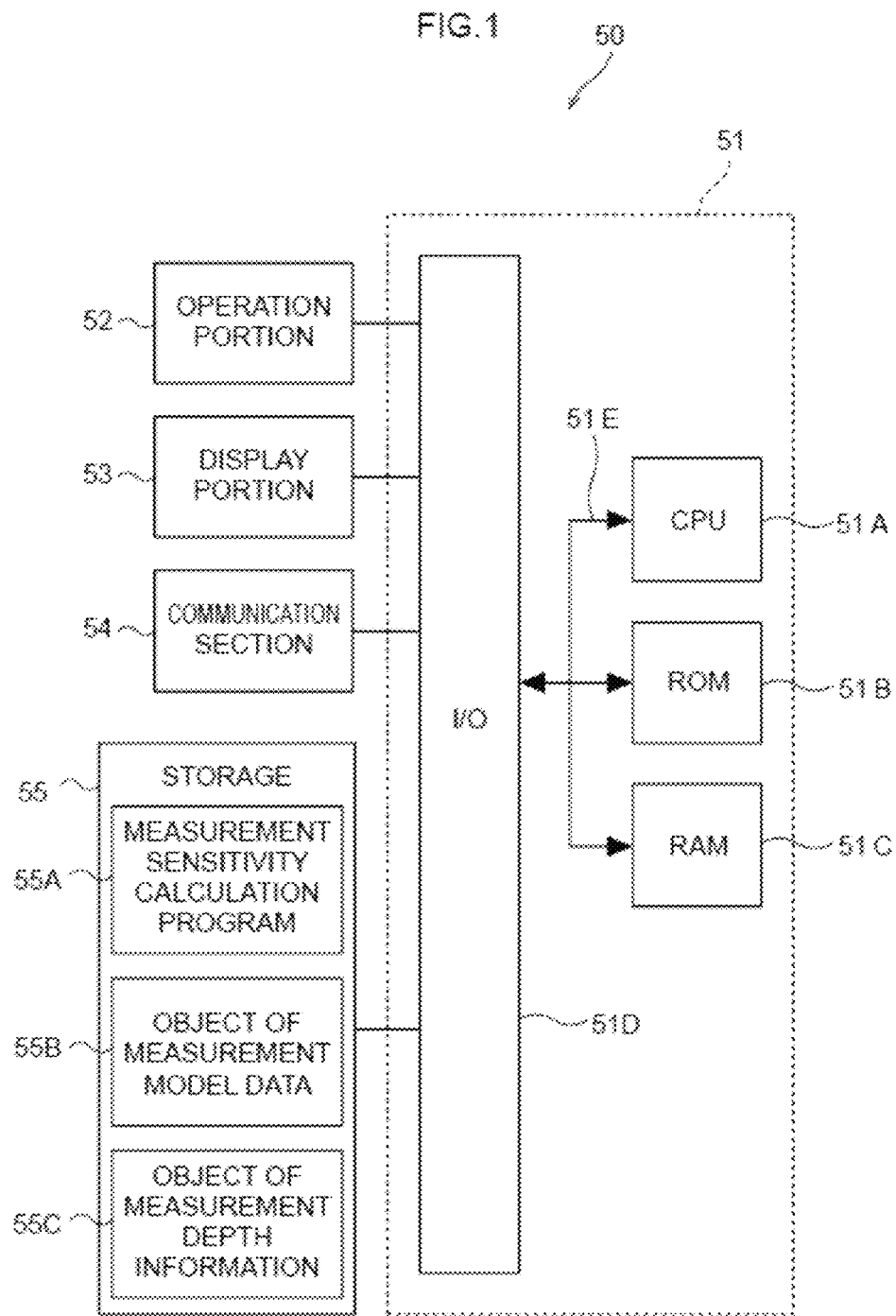
FIG. 1 is a structural drawing of a measurement sensitivity calculation device.

FIG. 1 is a drawing illustrating hardware structures of a measurement sensitivity calculation device 50. The measurement sensitivity calculation device 50 is a device including a general computer.

As illustrated in FIG. 1, the measurement sensitivity calculation device 50 has a controller 51. The controller 51 has a CPU (Central Processing Unit) 51A, a ROM (Read Only Memory) 51B, a RAM (Random Access Memory) 51C, and an input/output interface (I/O) 51D. Further, the CPU 51A, the ROM 51B, the RAM 51C and the I/O 51D are respectively connected via system bus 51E. The system bus 51E includes a control bus, an address bus and a data bus.

Further, an operation portion 52, a display portion 53, a communication section 54 and a storage 55 are connected to the I/O 51D.

The operation portion 52 is structured to include a mouse and a keyboard for example.

The display portion 53 is structured by a liquid crystal display or the like for example.

The communication section 54 is an interface for carrying out data communication with external devices.

The storage 55 is structured by a non-volatile, external storage device such as a hard disk or the like, and stores a measurement sensitivity calculation program 55A, object of measurement model data 55B, and object of measurement depth information 55C that are described later, and the like. The CPU 51A reads the measurement sensitivity calculation program 55A, which is stored in the storage 55, into the RAM 51C and executes the program.

The functional structures of the CPU 51A in a case in which the measurement sensitivity calculation device 50 executes the measurement sensitivity calculation program 55A are described next.

Figure 2:
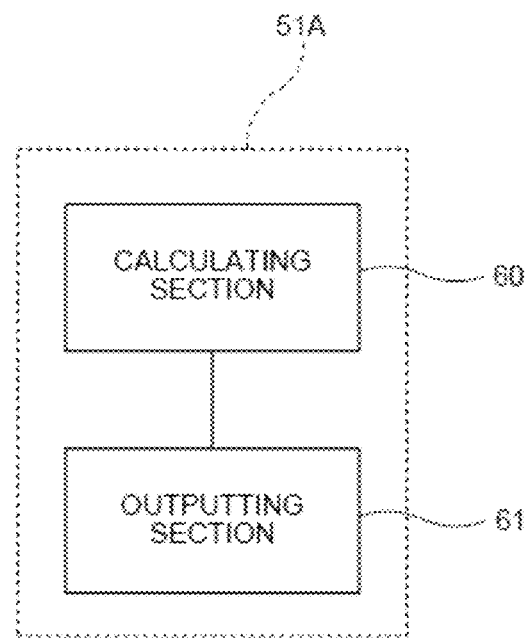
FIG. 2 is a functional block drawing of the measurement sensitivity calculation device.

As illustrated in FIG. 2, the CPU 51A functionally has a calculating section 60 and an outputting section 61.

The calculating section 60 calculates the measurement depth for each depth of an object of measurement, by using an object of measurement model that expresses the object of measurement. For example, the object of measurement is a body that absorbs light such as an organism, an agricultural product, wood, or the like. In the present embodiment, as an example, a case is described in which an organism is the object of measurement. However, the measurement sensitivity calculation device 50 is not limited to the field of medical equipment, and can be applied also to applications to products, services and the like in the field of rehabilitation and the field of sports science, and to quality management of various manufactured products such as agricultural products, timber, and the like.

The object of measurement model is a simulation model in which the layer structure, the light absorption coefficient, the light scattering coefficient and the like of the object of measurement are defined.

Figure 3:
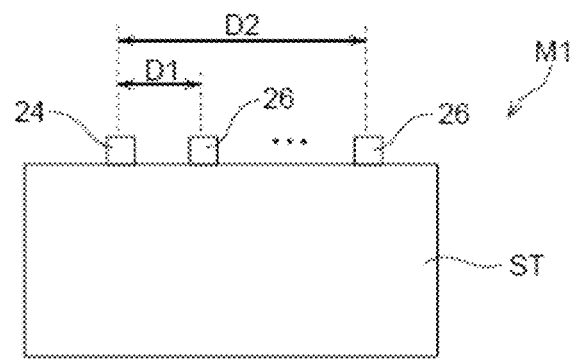
FIG. 3 is a drawing illustrating an example of an object of measurement model.

Object of measurement model M1 of gastrointestinal tissue that serves as the object of measurement is illustrated as an example in FIG. 3. As illustrated in FIG. 3, the layer structure of gastrointestinal tissue ST is a one layer structure.

In this case, at the object of measurement model M1 that expresses gastrointestinal tissue that is the object of measurement, the calculating section 60 calculates a first optical path length that expresses the length of a first optical path which is up to where the light, which is emitted from a light emitter 24 onto the gastrointestinal tissue, is received at a first light receiver 26 that is apart from the light emitter 24 by a first distance D1. Further, the calculating section 60 calculates the measurement sensitivity per object of measurement depth by using, as the measurement sensitivity, the optical path length difference between the first optical path length and a second optical path length that expresses the length of a second optical path that is up to where the light emitted from the light emitter 24 is received at the second light receiver 26 that is apart from the light emitter 24 by a second distance D2. Note that D1<D2, and, as an example, D1 and D2 are set to be less than or equal to several 10 mm (e.g., 40 mm).

Here, in the present embodiment, the object of measurement model M1 is a model that expresses the object of measurement by plural voxels as an example, although illustration thereof is omitted in FIG. 3. The present embodiment describes a case in which a cube whose one side is 0.5 mm as an example is used as the shape of the voxels, but the shape and the size of the voxels is not limited to this.

In this case, for each of the plural voxels, the calculating section 60 calculates the first optical path length and the second optical path length and calculates the measurement sensitivity, and integrates the measurement sensitivities calculated for the respective voxels of each depth of the object of measurement, and thereby calculates the measurement sensitivity per depth of the object of measurement.

The outputting section 61 outputs the measurement sensitivity that is calculated for each depth of the object of measurement. Specifically, the outputting section 61 displays on the display portion 53, or stores in the storage 55, the measurement sensitivity calculated for each depth of the object of measurement.

Figure 4:
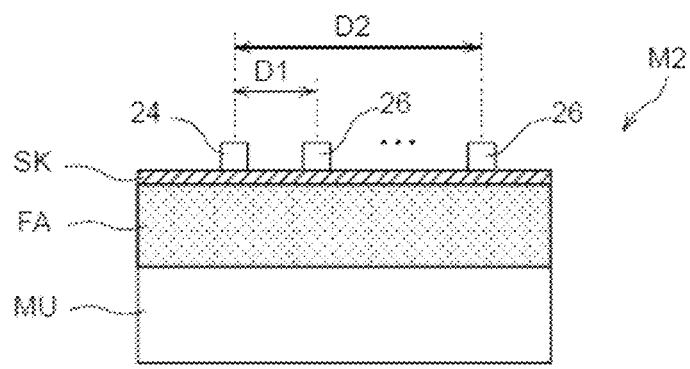
FIG. 4 is a drawing illustrating an example of an object of measurement model.

Object of measurement model M2 of a thigh muscle that serves as another example of the object of measurement is illustrated in FIG. 4. The layer structure of the thigh muscle is a three layer structure of skin SK, fat FA and muscle MU. Note that, in addition thereto, object of measurement models can be specified for various regions of the human body such as, for example, brain tissue, forearm muscle, and the like.

Note that, hereinafter, if the object of measurement model is not to be distinguished, it is called object of measurement model M.

Measurement sensitivity calculation processing that is executed at the CPU 51A is described next as operation of the present embodiment with reference to the flowchart illustrated in FIG. 5.

Figure 5:
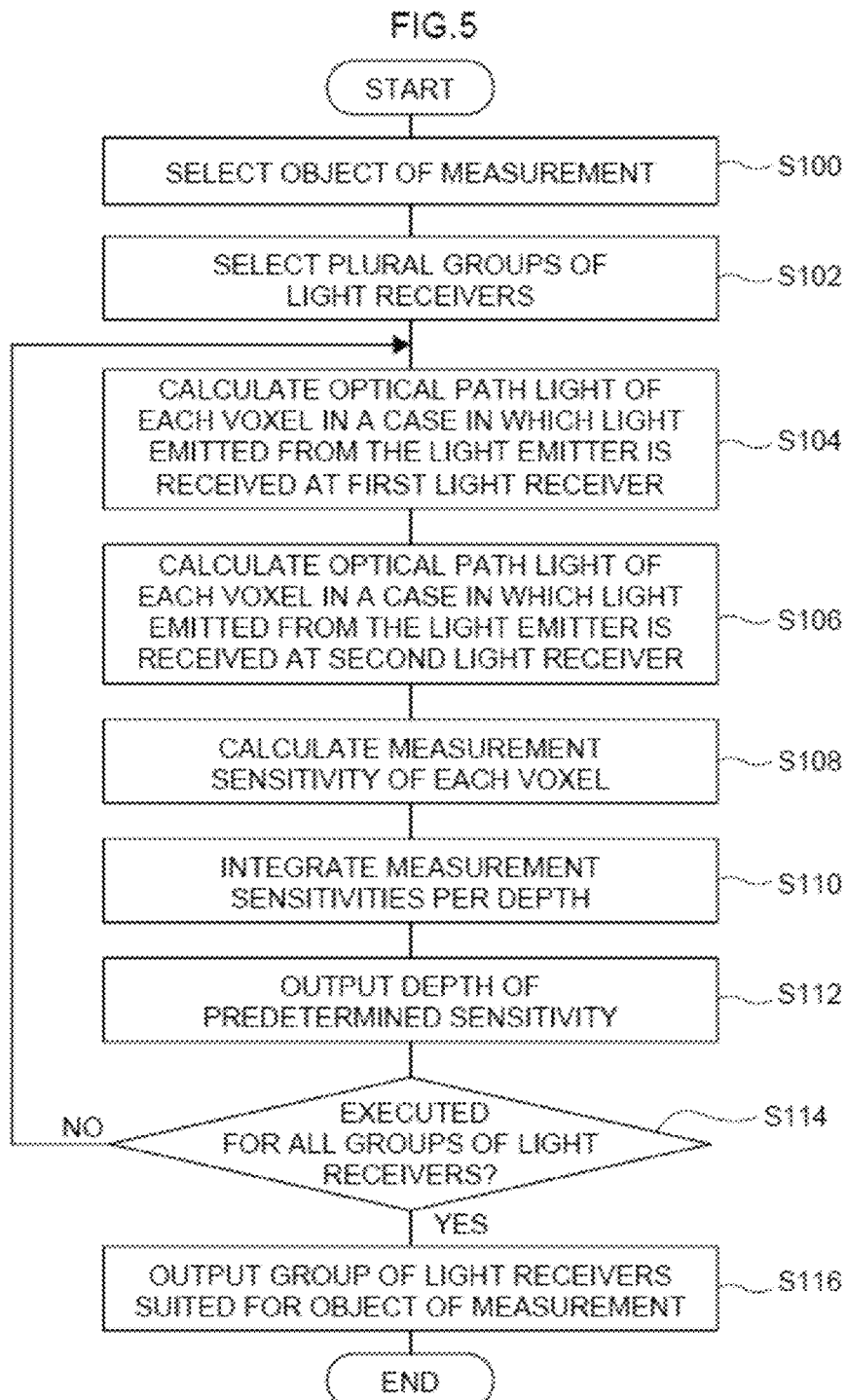
FIG. 5 is a flowchart of measurement sensitivity calculation processing.

As illustrated in FIG. 5, in step S100, a selection screen for a user to select an object of measurement is displayed on the display portion 53, and the selection of the object of measurement is received. Here, the user operates the operation portion 52 and selects the object of measurement for which calculation of the measurement sensitivity is desired, from among plural objects of measurement.

In step S102, a selection screen for selecting a group of the light receivers 26 is displayed on the display portion 53, and the selection of a group of the light receivers 26 is received. Here, the user operates the operation portion 52, and selects plural groups of two of the light receivers 26 that are combinations in which at least one of the first distance D1 and the second distance D2 is different. In the present embodiment, in order to simplify the calculation processing, the groups of the light receivers 26 that are thought to clearly be unrelated are removed from the plural groups of light receivers 26, and the user is made to select plural groups of the light receivers 26 that can be candidates in advance. Note that the processing of step S102 may be omitted, and the processings of steps S104~S114 may be executed for all of the plural groups of light receivers 26.

In step S104, the first optical path length, which expresses the length of the first optical path that is up to where the light, which is emitted from the light emitter 24 onto the object of measurement, is received at the first light receiver 26 that is apart from the light emitter 24 by the first distance D1, is calculated for each of the plural voxels.

The method of calculating the optical path length at each voxel is described hereinafter with reference to FIG. 6.

Figure 6:
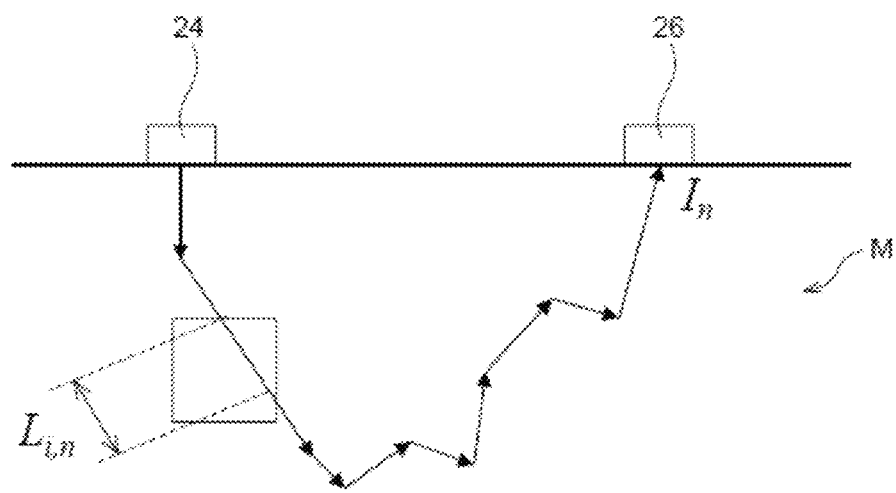
FIG. 6 is a drawing for explaining calculation of optical path length.

FIG. 6 schematically illustrates the optical path that is up until the light, which was emitted from the light emitter 24, is incident on the object of measurement and is received at the light receiver 26.

Description is given of the processes of determining average optical path length $L_i$ of the light that passes through an ith voxel $V_i$ by the Monte Carlo method.

It is assumed that, among the photon groups that are incident on the object of measurement model M, N photon groups reach the light receiver 26, and FIG. 6 shows the situation of movement of an nth photon group. The photon group has an intensity of 1 at the time of incidence, and that intensity is attenuated in accordance with the Lambert-Beer law in accordance with the absorption coefficient of the medium.

Further, at the time when the photon group changes direction due to scattering, the distance up until the direction is changed (the scattering distance) and the direction after the scattering are determined by using random numbers. Given that the scattering coefficient of the medium in which the photon group exists is μs, and that a uniform random number of 0 to 1 is R, −ln(R)/μs is the scattering distance.

Given that the optical path length at the time when the nth photon group passes within voxel $V_i$ while scattering is $L_{i,n}$, and that the intensity of that photon group at the time when the photon group reaches the light receiver 26 is $I_n$, the average optical path length $L_i$ of the photon groups that pass within voxel $V_i$ is expressed by the following formula.

$$L_i = \frac{\sum_{n=1}^{N} L_{i,n} I_n}{\sum_{n=1}^{N} I_n} \quad (1)$$

Namely, the average optical path length $L_i$ is obtained by weighted addition, by the intensities $I_n$ of the times when the photon groups reach the light receiver 26, of the optical path lengths $L_{i,n}$, of the times when the photon groups pass through voxel $V_i$, and division by the total sum of the light amounts of the photon groups that reach the light receiver 26. Note that the average optical path length is also simply called the optical path length.

In step S104, the optical path length $L_i$ of the first optical path is calculated from above formula (1) for all of the voxels $V_i$.

In step S106, the first optical path length, which expresses the length of the first optical path that is up to where the light, which is emitted from the light emitter 24 onto the object of measurement, is received at the second light receiver 26 that is apart from the light emitter 24 by the second distance D2, is calculated for each of the plural voxels. Similarly, the second optical path length, which expresses the length of the second optical path that is up to where the light, which is emitted from the light emitter 24 onto the object of measurement, is received at the second light receiver 26 that is apart from the light emitter 24 by the second distance D2, is calculated for each of the plural voxels.

Namely, in the same way as in step S104, the optical path length $L_i$ of the second optical path is calculated from above formula (1) for all of the voxels $V_i$.

In step S108, a measurement sensitivity $S_i$ is calculated for each voxel $V_i$. The measurement sensitivity $S_i$ is expressed by the following formula, where the first optical path length of voxel $V_i$ is $L_{i1}$, and the second optical path length is $L_{i2}$.

$$S_i = L_{i2} - L_{i1} \quad (2)$$

Namely, the calculation of the measurement sensitivity $S_i$ is the difference between the second optical path length $L_{i2}$ and the first optical path length $L_{i1}$.

In step S110, the measurement sensitivities $S_i$ of the respective voxels $V_i$ calculated in step S108 are integrated per depth. For example, the measurement sensitivities $S_i$ of the respective voxels $V_i$ are integrated per depth of 1 mm.

The measurement sensitivity per depth is thereby obtained. Note that the measurement sensitivities $S_i$ of the respective voxels $V_i$ may be integrated per 0.5 mm that is the length of one side of the voxel $V_i$, or the unit of the depth at which the measurement sensitivities $S_i$ are integrated can be set arbitrarily.

Figure 7:
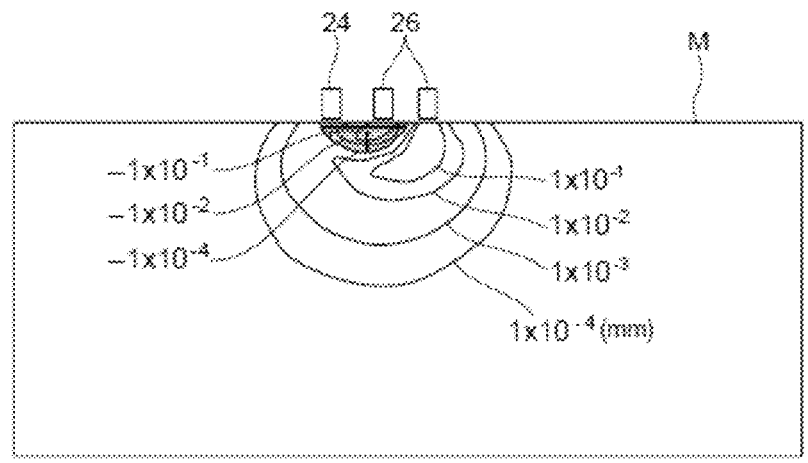
FIG. 7 is a drawing illustrating an example of measurement sensitivity distribution.

Examples of measurement sensitivity distributions are illustrated in isoline maps in FIGS. 7~10. FIG. 7 shows the measurement sensitivity distribution at a group of light receivers at which the first distance D1 is 3 mm and the second distance D2 is 5 mm. As illustrated in FIG. 7, positive measurement sensitivities of $1\times10^{-1}$ (mm)~$1\times10^{-4}$ (mm) are expressed by isolines, and negative measurement sensitivities of $-1\times10^{-1}$ (mm), $-1\times10^{-2}$ (mm), $-1\times10^{-4}$ (mm) are expressed by isolines. Here, the regions of negative measurement sensitivities are regions where measurement cannot be carried out accurately. Note that, in FIGS. 7~10, the measurement sensitivity distributions are expressed by isolines for convenience, but, as described above, the calculation of the actual measurement sensitivities is carried out by integrating the measurement sensitivities Si of the respective voxels $V_i$ per depth.

Similarly, FIG. 8 shows the measurement sensitivity distribution at a group of light receivers at which the first distance D1 is 5 mm and the second distance D2 is 7 mm.

Figure 9:
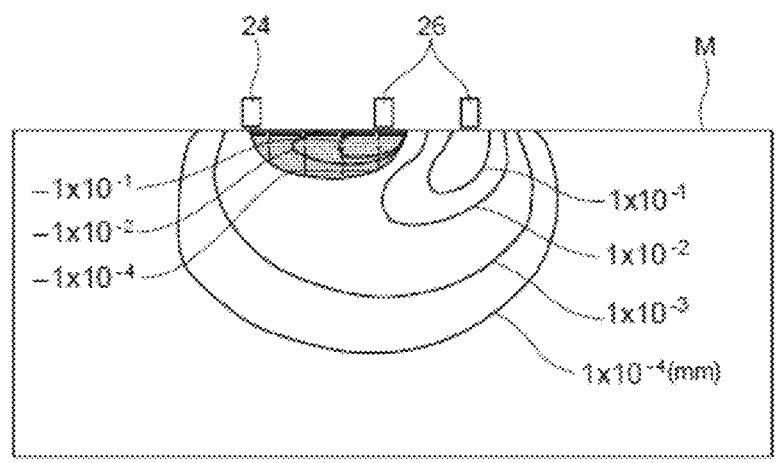
FIG. 9 is a drawing illustrating an example of measurement sensitivity distribution.

FIG. 9 shows the measurement sensitivity distribution at a group of light receivers at which the first distance D1 is 9 mm and the second distance D2 is 14 mm.

Figure 10:
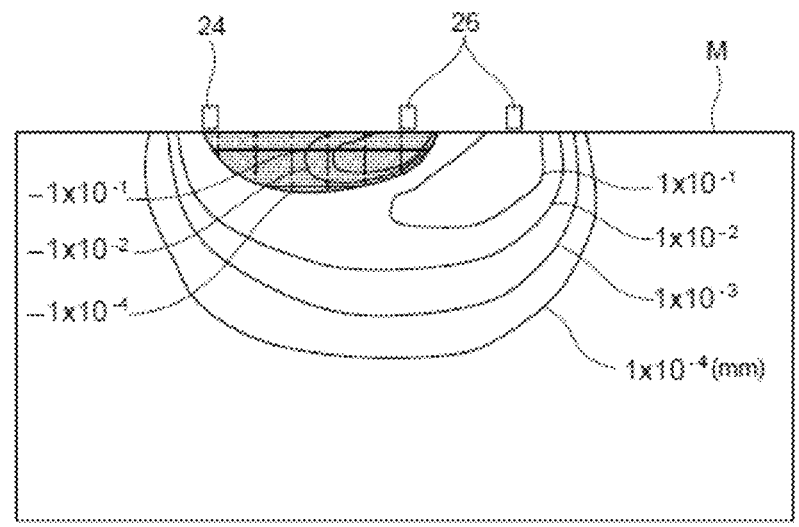
FIG. 10 is a drawing illustrating an example of measurement sensitivity distribution.

FIG. 10 shows the measurement sensitivity distribution at a group of light receivers at which the first distance D1 is 20 mm and the second distance D2 is 30 mm.

Further, graphs of measurement sensitivities corresponding to FIGS. 7~10 are illustrated in FIGS. 11~15, respectively. FIG. 7 is a graph of measurement sensitivity corresponding to FIG. 11, and the horizontal axis is depth (mm), and the vertical axis is measurement sensitivity.

Figure 11:
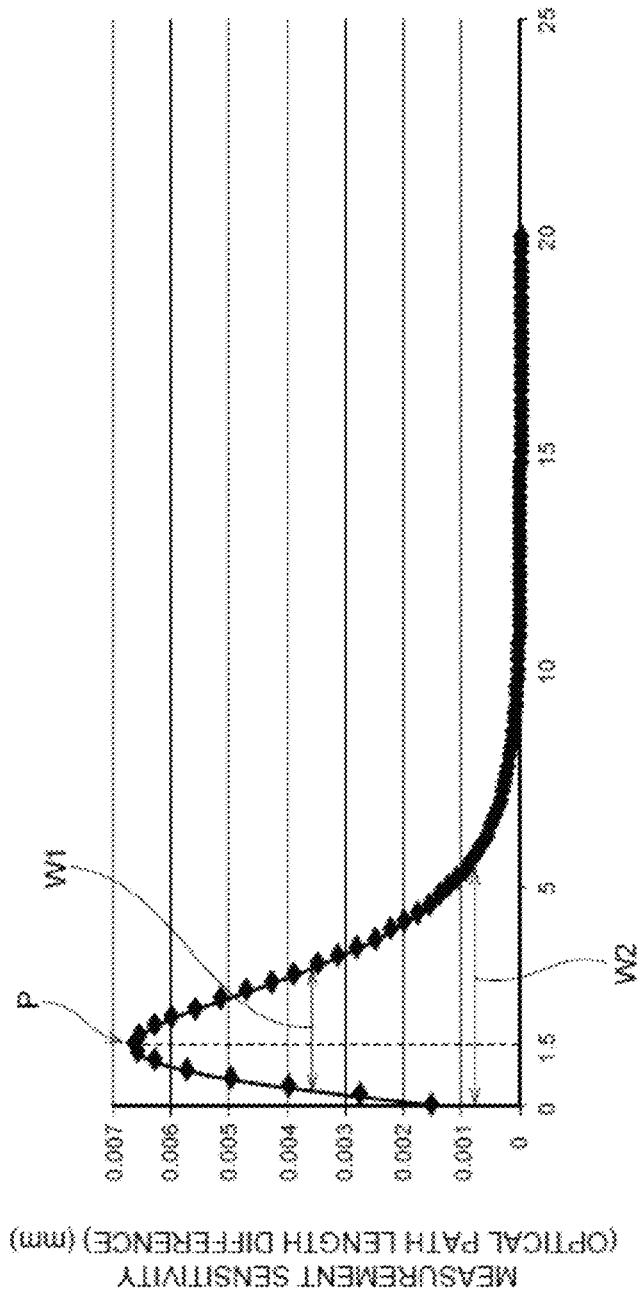
FIG. 11 is a graph illustrating the relationship between measurement sensitivity and depth.

As illustrated in FIG. 11, at the group of light receivers at which D1=3 mm and D2=5 mm, the depth at which the measurement sensitivity becomes peak value P is approximately 1.5 mm. Further, the range of the depths of half-value width W1 of the measurement sensitivity, i.e., depths at which the measurement sensitivity becomes ½ of the peak value, is 0.3~3.6 mm. Further, the range of the depths of 1/10 width W2, i.e., depths at which the measurement sensitivity becomes 1/10 of the peak value, is 0~6.2 mm.

Figure 12:
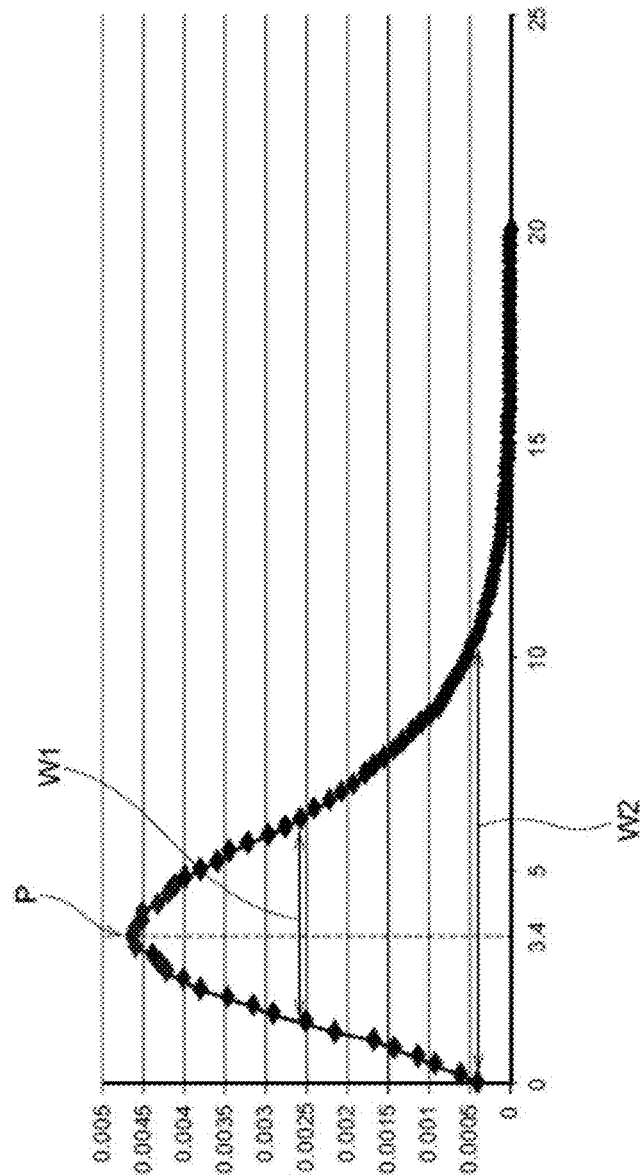
FIG. 12 is a graph illustrating the relationship between measurement sensitivity and depth.

Further, as illustrated in FIG. 12, at the group of light receivers at which D1=5 mm and D2=7 mm, the depth at which the measurement sensitivity becomes the peak value P is approximately 3.4 mm. Further, the range of the depths of the half-value width W1 of the measurement sensitivity is 1.2~6.4 mm. Further, the range of the depths of 1/10 width W2 is 0.2~10.4 mm.

Figure 13:
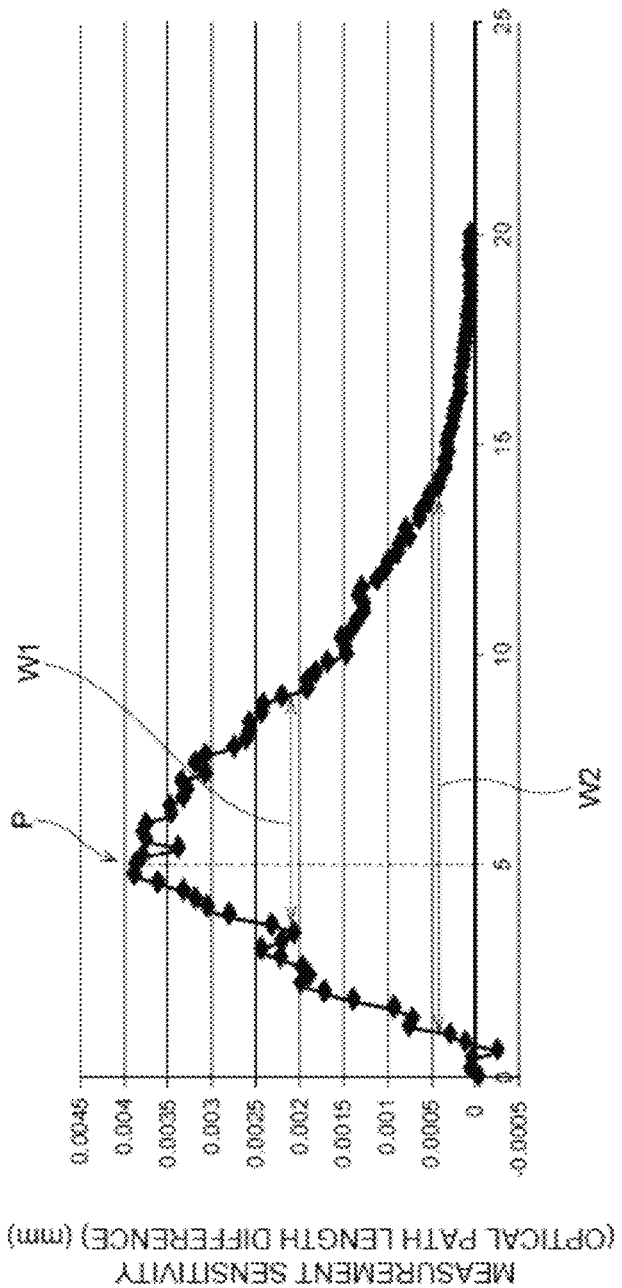
FIG. 13 is a graph illustrating the relationship between measurement sensitivity and depth.

Further, as illustrated in FIG. 13, at the group of light receivers at which D1=9 mm and D2=14 mm, the depth at which the measurement sensitivity becomes the peak value P is approximately 5 mm. Further, the range of the depths of the half-value width W1 of the measurement sensitivity is 2.2~9 mm. Further, the range of the depths of 1/10 width W2 is 0.9~14 mm.

Figure 14:
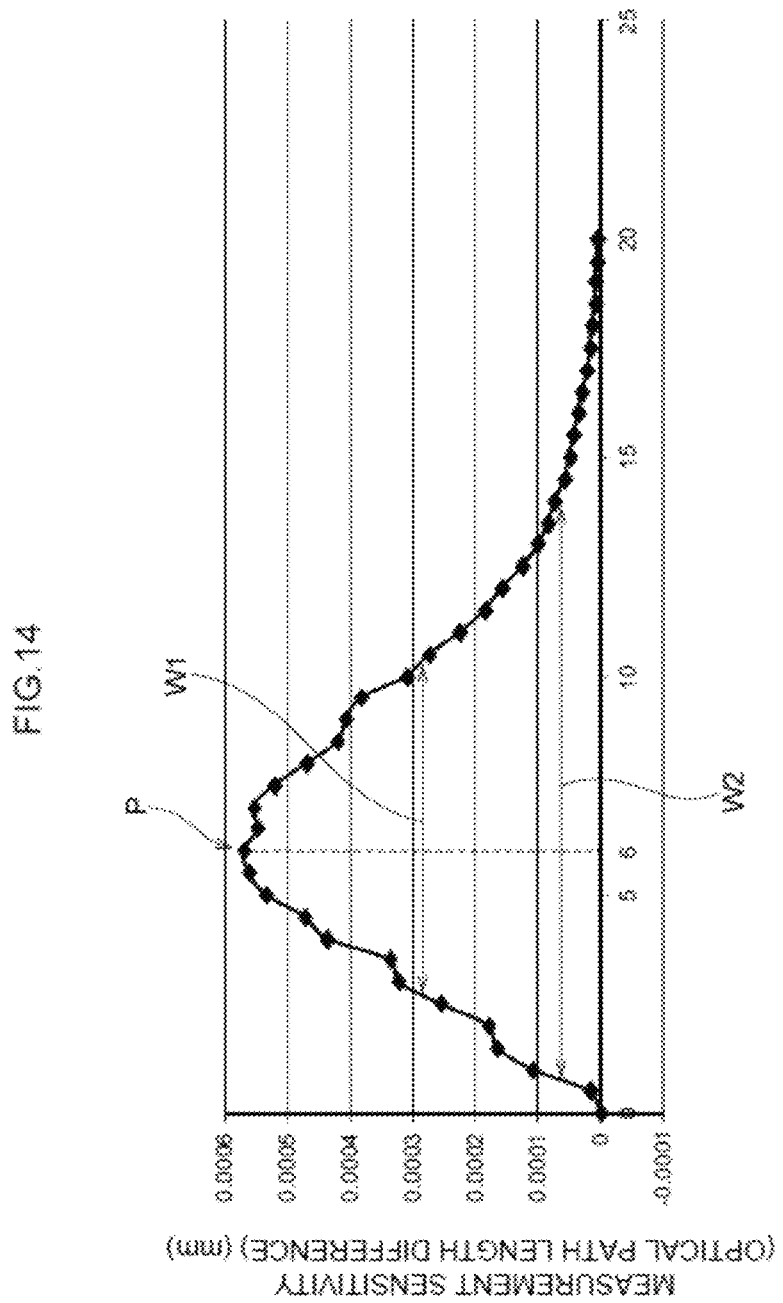
FIG. 14 is a graph illustrating the relationship between measurement sensitivity and depth.

Further, as illustrated in FIG. 14, at the group of light receivers at which D1=20 mm and D2=30 mm, the depth at which the measurement sensitivity becomes the peak value P is approximately 6 mm. Further, the range of the depths of the half-value width W1 of the measurement sensitivity is 2.6~10.5 mm. Further, the range of the depths of 1/10 width W2 is 0.8~14.5 mm.

In this way, it can be understood that, when the first distance D1 and the second distance D2 are different, the peak value of the measurement sensitivity differs. Specifically, it can be understood that, as the first distance D1 and the second distance D2 become long, the depth of the peak value of the measurement sensitivity gradually shifts in the direction of becoming deeper.

In step S112, the depth of a predetermined sensitivity is outputted. Namely, the depth of a predetermined sensitivity is displayed on the display portion 53 or stored in the storage 55. Here, the depth of a predetermined sensitivity can be, for example, the depth at which the measurement sensitivity becomes the peak value, the depths of a range in which the measurement sensitivity becomes the half-value width, the depths of a range in which the measurement sensitivity becomes 1/10 width, or the like, but depths of the measurement sensitivity that are other than these may be outputted.

In step S114, it is judged whether or not the processings of steps S104~S112 have been executed for all of the groups of light receivers that were selected in step S102. If the processings have been executed for all of the groups of light receivers, the routine moves on to step S116. On the other hand, if the processings have not been executed for all of the groups of light receivers, the routine returns to step S104, and the processings of steps S104~S112 are executed for the groups of light receivers for which execution has not yet been carried out.

In step S116, the first distance D1 and the second distance D2 at the group of light receivers that are suited to the object of measurement are outputted. Specifically, first, by referring to the object of measurement depth information 55C, the depth of the object of measurement that was selected in step S100 is acquired. The object of measurement depth information 55C is information of depths of various types of objects of measurement. Then, for example, among the plural groups of the light receivers 26, the first distance D1 and the second distance D2 at a group of the light receivers 26, at which the depth of the object of measurement is included in the range of depths corresponding to a measurement sensitivity of greater than or equal to a threshold value that is determined in advance, are outputted. For example, the threshold value may be a measurement sensitivity that is slightly smaller than the peak value (e.g., a measurement sensitivity that is several percent smaller than the peak value), or may be the measurement sensitivity of the half-value width, i.e., ½ of the peak value, or, depending on the application of the measurement, may be the measurement sensitivity of the 1/10 width, i.e., 1/10 of the peak value. Specifically, for example, in a case in which the threshold value is made to be ½ of the peak value, and the depth of the object of measurement is 10 mm, the group of light receivers 26 at which the depth of 10 mm is included in the range of depths corresponding to measurement sensitivities of greater than or equal to ½ of the peak value, is the group of D1=20 mm and D2=30 mm that is illustrated in FIG. 14. Accordingly, this group is selected as the light receiver 26 group that is suitable for the object of measurement.

For example, in a case in which the object of measurement is the intestinal wall, the group of the light receivers 26 of D1=3 mm and D2=5 mm is suitable. Further, in a case in which the object of measurement is the stomach or the esophagus, the group of the light receivers 26 of D1=5 mm and D2=7 mm is suitable. Further, in a case in which the object of measurement is muscle tissue, the group of the light receivers 26 of D1=20 mm and D2=30 mm is suitable.

In this way, in the present embodiment, the measurement sensitivity per voxel is calculated by using a measurement sensitivity model in which an object of measurement is expressed by plural voxels, and the measurement sensitivities are integrated per depth, and the measurement sensitivity per depth is thereby calculated. Due thereto, the measurement sensitivity of the object of measurement can be calculated accurately per depth, and the group of light receivers that is suited to the object of measurement can be specified easily. Further, in the present embodiment, because the measurement sensitivity per depth of the object of measurement is calculated by using the optical path length difference as the measurement sensitivity, the efficiency of calculation improves. Note that the method of calculating the optical path length that was described in steps S104, S106 is an example. Because the absorption coefficient, the scattering coefficient and the like differ due to differences in the number of layers and the medium of the object of measurement model, it is preferable to calculate the optical path length by using a method of calculating the optical path length that corresponds to the object of measurement model.

Second Embodiment

A second embodiment is described next.

Figure 15:
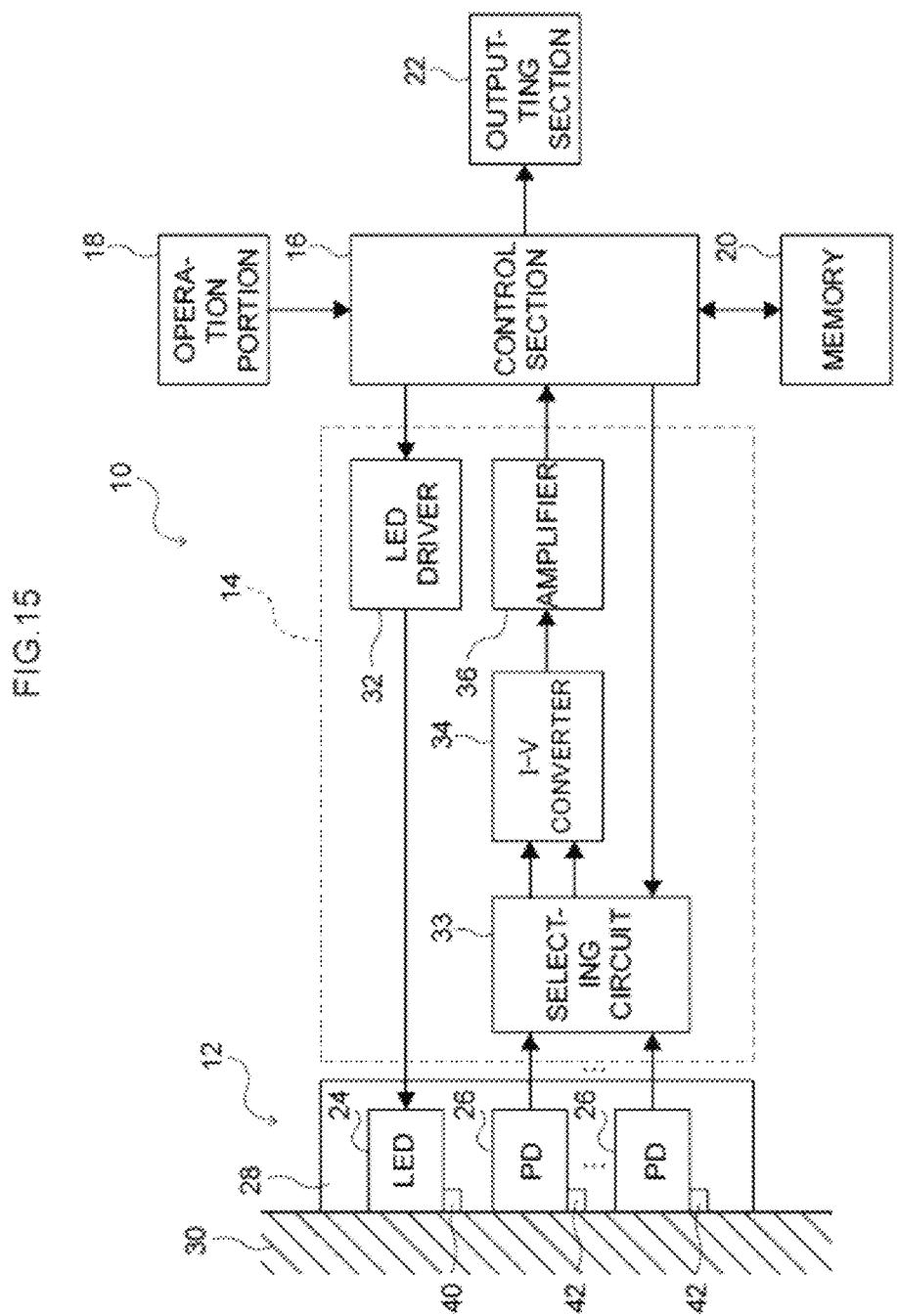
FIG. 15 is a structural drawing of an optical measurement device.

The schematic structure of an optical measurement device 10 is illustrated in FIG. 15. As illustrated in FIG. 15, the optical measurement device 10 is structured to include a probe 12, a driving device 14, a control section 16, an operation portion 18, a memory 20 and an outputting section 22.

The probe 12 is a structure in which the light emitter 24, the plural light receivers 26, a light emitter 40 for ToF and two light receivers 42 for ToF are provided on a member (e.g., a member having rubber-like characteristics) 28 that is shaped as a flat plate and is flexible for example. In the present embodiment, as an example, a light-emitting diode (LED) is used as the light emitter 24, and photodiodes are used as the light receivers 26. The probe 12 is provided so as to be attached to an endoscope, and more specifically, the forceps tip of an endoscope, that is used in surgeries for, for example, esophageal cancer, stomach cancer or the like. In this case, the optical measurement device 10 measures the oxygen concentration or the like in a state in which the probe 12 is made to abut an object of measurement 30 such as the tube of the esophagus, or the stomach wall or the like. The oxygen concentration or the like that is measured is taken into consideration in cases such as determining to how far the tube of the esophagus or the stomach wall is to be resected.

In the present embodiment, as an example, the light emitter 24 is a light-emitting diode of two wavelengths whose peak wavelengths are a first wavelength λ1 and a second wavelength λ2. The first wavelength λ1 and the second wavelength λ1 are set to two different wavelengths at which there is little absorption by hemoglobin and water, and specifically, in the range of from 700 nm to 900 nm. In the present embodiment, as an example, the first wavelength λ1 is 770 nm, and the second wavelength 22 is 830 nm.

The light emitter 24 and the respective light receivers 26 are disposed at respectively different separated intervals, and three or more of the light receivers 26 are disposed in a row. These three or more light receivers 26 are selected as a group of light receivers that are suited for the object of measurement, which group is obtained by the measurement sensitivity calculation device 50, which was described in the first embodiment, executing the measurement sensitivity calculation processing of FIG. 5. Namely, the distances of the three or more light receivers 26 to the light emitter 24 are distances suited to the object of measurement that is to be measured by the optical measurement device 10.

The light emitter 40 for ToF emits pulse light for measuring the Time of Flight (ToF) of the light. The light emitter 40 for ToF is provided in a vicinity of the light emitter 24.

The two light receivers 42 for ToF receive the light that is emitted from the light emitter 40 for ToF. The two light receivers 42 for ToF are provided in respective vicinities of two of the light receivers 26 that are determined in advance among the plural light receivers 26. Namely, the light emitter 40 for ToF and the two light receivers 42 for ToF are disposed in the same positional relationship as the positional relationship of the light emitter 24 and two of the light receivers 26. Note that the light emitter 40 for ToF and the two light receivers 42 for ToF are an example of the measuring section.

The driving device 14 is structured to include an LED driver 32, a selecting circuit 33, an I-V converter 34, and an amplifier 36.

Due to an instruction from the control section 16, the LED driver 32 causes the light emitter 24 to emit lights of predetermined wavelengths and a predetermined light intensity.

Due to an instruction from the control section 16, the selecting circuit 33 selects two light receivers 26, and outputs the output from the two, selected light receivers 26 to the I-V converter 34.

The I-V converter 34 converts, into voltages, the currents that are obtained by photoelectrically converting the lights received at the light receivers 26 selected by the selecting circuit 33, and outputs the voltages to the amplifier 36.

The amplifier 36 amplifies the voltages, which were converted by the I-V converter 34, to voltages of a predetermined level, and outputs the amplified voltages to the control section 16 as signals expressing the light intensities.

The control section 16 instructs the selecting circuit 33 to select two of the light receivers 26, and instructs the LED driver 32 to cause the light emitter 24 to emit light, and, on the basis of the light intensities of the lights received at the two, selected light receivers 26 that were obtained as a result thereof, calculates hemoglobin concentrations or the like. The results of calculation are outputted to the outputting section 22. The outputting section 22 is structured by a display or a printer or the like for example, and outputs the results of calculation by displaying or printing.

The program of a measurement processing routine that is described later, and data that is used in that processing and relates to the results of simulations executed in advance, and the like are stored in advance in the memory 20.

Figure 16:
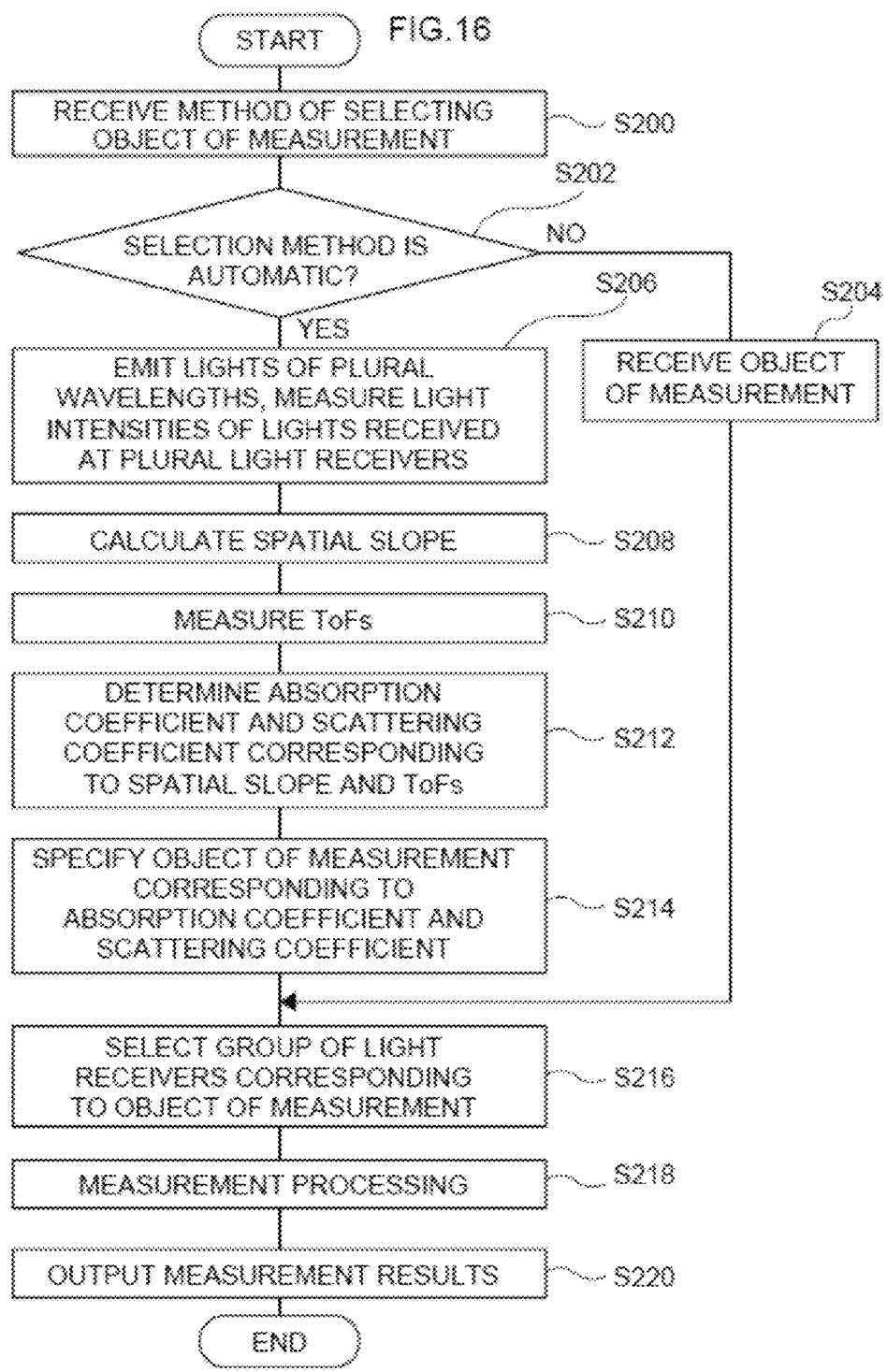
FIG. 16 is a flowchart of measurement processing.

The measurement processing that is executed at the control section 16 is described next as the operation of the present embodiment, with reference to the flowchart illustrated in FIG. 16.

At the time of measurement, the start of measurement is instructed due to the probe 12 being made to contact the object of measurement of the subject who is to be measured, and the operation portion 18 being operated. Due thereto, the processing illustrated in FIG. 16 is started.

In step S200, the method of selecting the object of measurement is received. The user operates the operation portion 18 and gives an instruction as to whether the object of measurement is to be selected automatically or is to be selected manually.

In step S202, it is judged whether or not the selection method received in step S200 is automatic. If the selection method is manual, the routine moves on to step S204, and if the selection method is automatic, the routine moves on to step S206.

In step S204, the object of measurement is received. Here, by operating the operation portion 18, the user manually instructs the object of measurement for which measurement is desired. After the object of measurement is received, the routine moves on to step S216.

In step S206, lights of the first wavelength λ1 and the second wavelength 22 are successively made to be emitted from the light emitter 24, and the light intensities of the lights received at the two, predetermined light receivers 26 are respectively obtained.

In step S208, on the basis of the light intensities acquired in step S206, the spatial slope in the spatial resolution technique is calculated. A known method described in U.S. Pat. No. 5,062,698 or the like for example is used in calculating the spatial slope.

In step S210, the light emitter 40 for ToF is made to emit light, and the ToFs until the emitted light is received at the light receivers 42 for ToF is measured.

In step S212, the absorption coefficient and the scattering coefficient, which correspond to the spatial slope calculated in step S208 and the ToFs measured in step S210, are determined. For example, table data, which is determined in advance from a logic analysis database or the like and which expresses the relationships of correspondence between spatial slopes and ToFs, and absorption coefficients and scattering coefficients, is stored in advance in the memory 20. The absorption coefficient and the scattering coefficient, which correspond to the spatial slope calculated in step S208 and the ToFs measured in step S210, are determined by referring to this table data.

In step S214, the object of measurement that corresponds to the absorption coefficient and the scattering coefficient that were determined in step S212 is specified. For example, table data, which expresses the relationships of correspondence between absorption coefficients and scattering coefficients, and objects of measurement, is stored in advance in the memory 20. The object of measurement that corresponds to the absorption coefficient and scattering coefficient determined in step S212 is specified by referring to this table data. Due thereto, the object of measurement can be specified automatically, without the user manually designating the object of measurement.

In step S216, the group of light receivers that corresponds to the object of measurement specified in step S214 is selected. For example, table data, which expresses the relationships of correspondence between objects of measurement and light receiver groups, is stored in advance in the memory 20. The group of light receivers corresponding to the object of measurement specified in step S214 is determined by referring to this table data, and the selecting circuit 33 is instructed to select the light receivers 26 of the determined group.

In step S218, measurement processing is executed. Namely, lights of the first wavelength λ1 and the second wavelength λ2 are made to be emitted successively from the light emitter 24, and the light intensities of the lights received at the two light receivers 26 that were selected in step S216 are respectively acquired. Then, the absorption degrees of the lights are computed on the basis of the acquired light intensities. Further, the hemoglobin concentration or the like is calculated on the basis of the absorption degrees of the lights. A known method described in U.S. Pat. No. 5,062,698 or the like for example can be used in calculating the absorption degrees of the lights and the hemoglobin concentration or the like.

In step S220, the results of measurement of step S218 are outputted by the outputting section 22.

Because the object of measurement can be specified automatically in this way, the work of the user manually designating the object of measurement can be eliminated. Further, because it is also possible for the user to manually designate the object of measurement, the convenience improves.

Note that the second embodiment describes a structure in which the two light receivers 42 for ToF are provided respectively in vicinities of the two, predetermined light receivers 26 among the plural light receivers 26, but there may be a structure in which one light receiver 42 for ToF is provided. In this case, the one light receiver 42 for ToF is disposed at a position that takes balance into consideration, so as to be close to both of the two, predetermined light receivers 26. Specifically, the light receiver 42 for ToF may be provided at an intermediate position between the two, predetermined light receivers 26. Namely, the light receiver 42 for ToF may be provided at a position at which the distance thereto from each of the two, predetermined light receivers 26 is equal. Due thereto, an average scattering coefficient that is close to the scattering coefficients corresponding to the two optical paths from the light emitter 24 to the two, predetermined light receivers 26 can be determined, and this is therefore preferable. Further, there may be a structure in which, in FIG. 15, only one of the light receiver 42 for ToF that is adjacent to the light receiver 26 that is positioned in the middle, and the light receiver 42 for ToF that is adjacent to the lowest light receiver 26, is provided.

Third Embodiment

A third embodiment is described next. The third embodiment describes results of simulating measurement sensitivity with plural combinations of the first distance D1 and the second distance D2.

Figure 17:
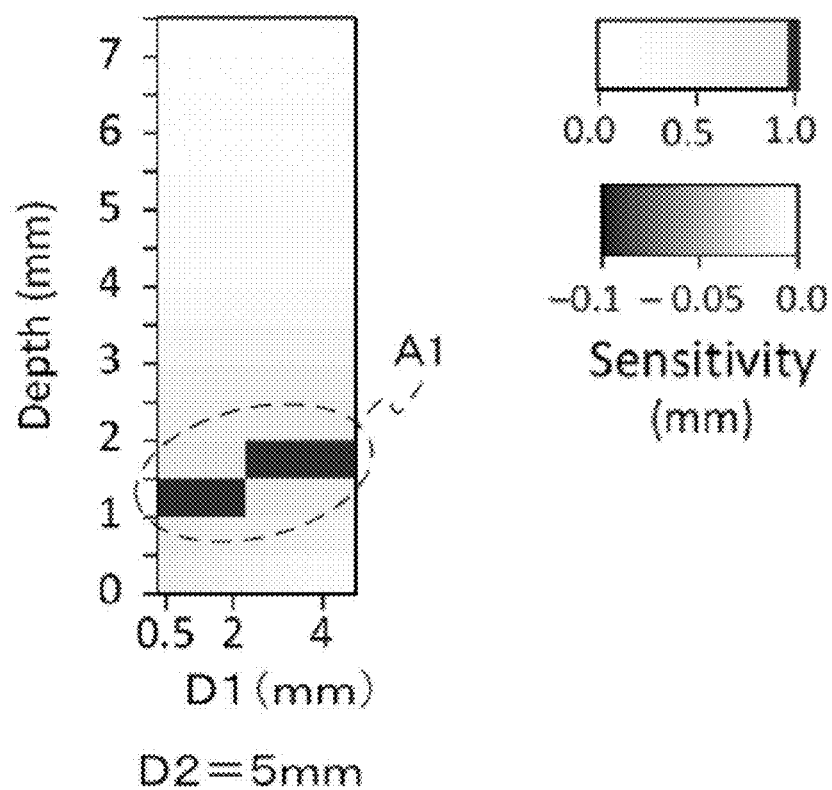
FIG. 17 is a drawing illustrating results of a simulation of measurement sensitivity per measurement depth in a case in which the object of measurement is skin tissue and a second distance D2 is 5 mm.

FIG. 17 illustrates results of simulating the measurement sensitivity (Sensitivity) per measurement depth (Depth) by using an object of measurement model of skin tissue (including subcutaneous tissue) as the object of measurement, with the second distance D2 being 5 mm and the first distance D1 being made variable within the range of 0 (mm)<D1<5 (mm). As illustrated in FIG. 17, the measurement sensitivity assumes a value in the range of −1.0~1.0, and positive sensitivities and negative sensitivities are shown in different colors, and the measurement sensitivity is expressed by gradations whose density changes in accordance with the value.

As illustrated in FIG. 17, of region A1 that is circled by the dashed line, the regions where the color is dark are the peak measurement sensitivity. Here, the peak measurement sensitivity is the measurement sensitivity at which the measurement sensitivity is 1 (mm). As illustrated in FIG. 17, it can be understood that the measurement sensitivity is peak in the range in which the measurement depth is greater than or equal to 1 (mm) and less than or equal to 2 (mm).

Note that, in FIG. 17, there is no region of negative measurement sensitivity. Namely, there is no combination of the first distance D1 and measurement-sensitivity depth at which the measurement sensitivity is negative.

Figure 18:
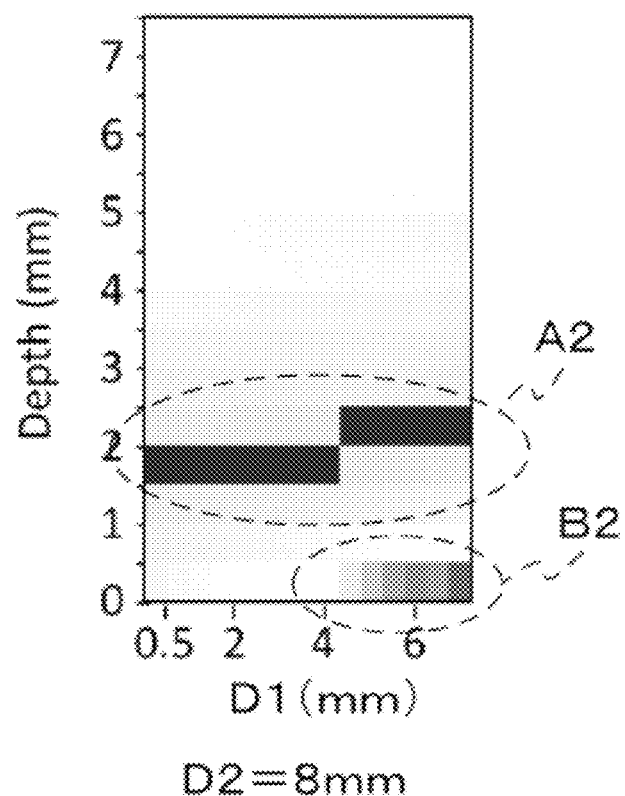
FIG. 18 is a drawing illustrating results of a simulation of measurement sensitivity per measurement depth in a case in which the object of measurement is skin tissue and the second distance D2 is 8 mm.

FIG. 18 illustrates results of simulating the measurement sensitivity per measurement depth under conditions that are similar to those of FIG. 17, except that the second distance D2 is 8 mm and the first distance D1 is variable within the range of 0 (mm)<D1<8 (mm).

As illustrated in FIG. 18, of region A2 that is circled by the dashed line, the regions where the color is dark are the peak measurement sensitivity. As illustrated in FIG. 18, it can be understood that the measurement sensitivity is peak in the range in which the measurement depth is greater than or equal to 1.5 (mm) and less than or equal to 2.5 (mm).

Note that, in FIG. 18, the measurement sensitivity is negative in region B2 that is circled by the dashed line.

Figure 19:
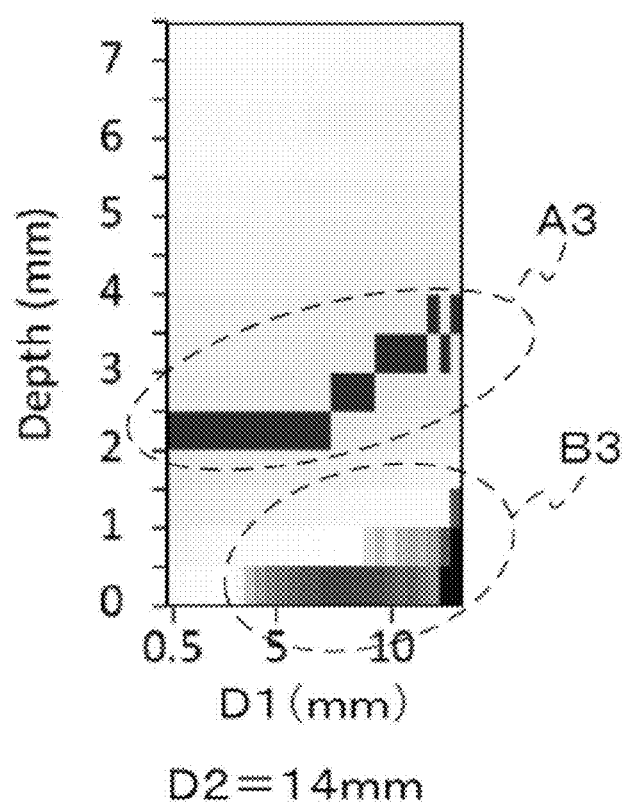
FIG. 19 is a drawing illustrating results of a simulation of measurement sensitivity per measurement depth in a case in which the object of measurement is skin tissue and the second distance D2 is 14 mm.

FIG. 19 illustrates results of simulating the measurement sensitivity per measurement depth under conditions that are similar to those of FIG. 17, except that the second distance D2 is 14 mm and the first distance D1 is variable within the range of 0 (mm)<D1<14 (mm).

As illustrated in FIG. 19, of region A3 that is circled by the dashed line, the regions where the color is dark are the peak measurement sensitivity. As illustrated in FIG. 19, it can be understood that the measurement sensitivity is peak in the range in which the measurement depth is greater than or equal to 2.0 (mm) and less than or equal to 4.0 (mm).

Note that, in FIG. 19, the measurement sensitivity is negative in region B3 that is circled by the dashed line.

Figure 20:
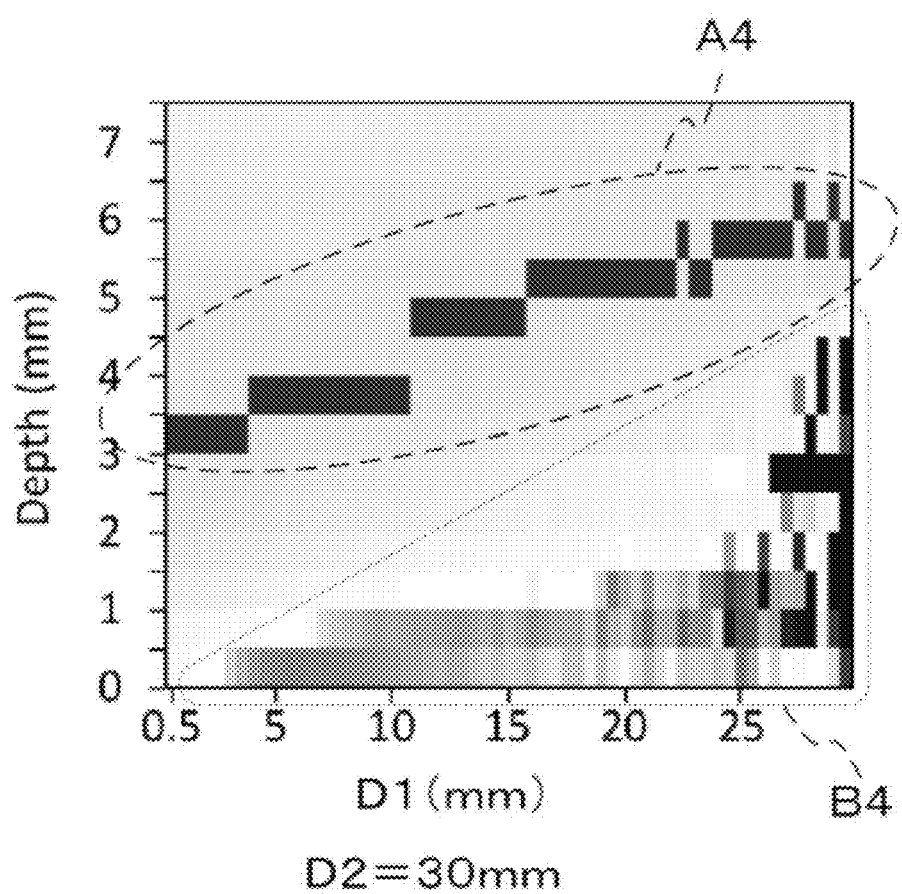
FIG. 20 is a drawing illustrating results of a simulation of measurement sensitivity per measurement depth in a case in which the object of measurement is skin tissue and the second distance D2 is 30 mm.

FIG. 20 illustrates results of simulating the measurement sensitivity per measurement depth under conditions that are similar to those of FIG. 17, except that the second distance D2 is 30 mm and the first distance D1 is variable within the range of 0 (mm)<D1<30 (mm).

As illustrated in FIG. 20, of region A4 that is circled by the dashed line, the regions where the color is dark are the peak measurement sensitivity. As illustrated in FIG. 20, it can be understood that the measurement sensitivity is peak in the range in which the measurement depth is greater than or equal to 3.0 (mm) and less than or equal to 6.5 (mm).

Note that, in FIG. 20, the measurement sensitivity is negative in region B4 that is circled by the dashed line.

From the results of FIGS. 17-20, in the measurement processing at the optical measurement device 10 illustrated in FIG. 15 for example, it is preferable to, in a case in which the object of measurement is skin tissue and the depth of the object of measurement is greater than or equal to 1 mm and less than or equal to 3 mm, select the second light receiver 26 whose second distance D2 is less than or equal to 14 mm.

Further, the present inventors carried out simulations that were similar to those of FIGS. 17~20 also for various second distances D2 other than the second distances D2 shown in FIGS. 17~20. Then, from the results of the simulations shown in FIGS. 17~20 and the results of the simulations other than FIGS. 17~20, the present inventors understood that the measurement depth becomes deeper as the first distance D1 and the second distance D2 become longer.

Further, it was understood that the following formula is established, given that Dp is the measurement depth.

$$Dp \approx D2/5 \qquad (3)$$

wherein $D1 \approx D2/2$.

Namely, in a case in which the first distance D1 is approximately half of the second distance D2, the measurement depth Dp is approximated by ⅕ of the second distance D2. Specifically, as the result of carrying out regression analysis, it was understood that the relationship of correspondence among the measurement depth Dp1, the first distance D1 and the second distance D2 is expressed by the following formula.

$$Dp1 = 0.090 \times D1 + 0.079 \times D2 + 0.85 \qquad (4)$$

Accordingly, in the measurement processing at the optical measurement device 10 illustrated in FIG. 15 for example, in a case in which the object of measurement is skin tissue, the first light receiver 26 and the second light receiver 26 corresponding to the first distance D1 and the second distance D2 that are nearest to the first distance D1 and the second distance D2, which satisfy the conditions that the first distance D1 is ½ of the second distance D2 and that the depth of the skin tissue at which measurement is desired is ⅕ of the second distance D2, may be selected.

Further, in the measurement processing at the optical measurement device 10 illustrated in FIG. 15 for example, the first light receiver 26 and the second light receiver 26 may be selected on the basis of the relationship of correspondence among the depth of the object of measurement, the first distance and the second distance, which relationship of correspondence is derived on the basis of the calculation results of calculating the measurement sensitivity per depth of the object of measurement. For example, the first light receiver 26 and the second light receiver 26 may be selected on the basis of above formula (4).

Figure 21:
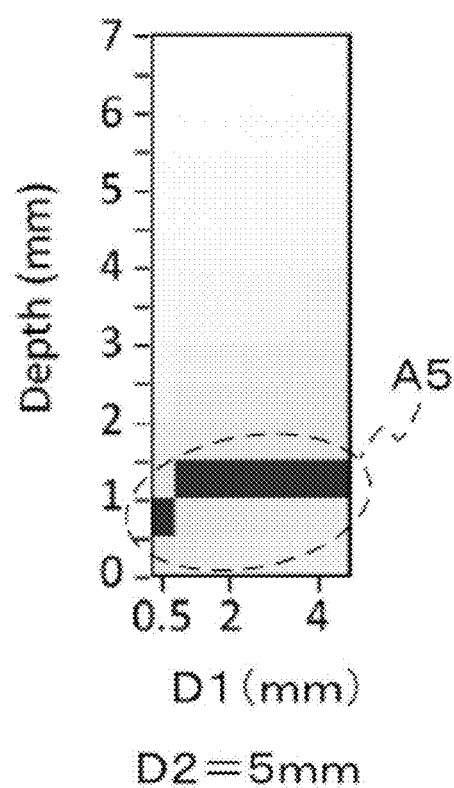
FIG. 21 is a drawing illustrating results of a simulation of measurement sensitivity per measurement depth in a case in which the object of measurement is gastrointestinal tissue and the second distance D2 is 5 mm.

FIG. 21 illustrates results of simulating the measurement sensitivity per measurement depth, by using an object of measurement model of gastrointestinal tissue that serves as the object of measurement, and under conditions that are similar to those of FIG. 17 except that the second distance D2 is 5 mm and the first distance D1 is variable within the range of 0 (mm)<D1<5 (mm).

As illustrated in FIG. 21, of region A5 that is circled by the dashed line, the regions where the color is dark are the peak measurement sensitivity. As illustrated in FIG. 21, it can be understood that the measurement sensitivity is peak in the range in which the measurement depth is greater than or equal to 0.5 (mm) and less than or equal to 1.5 (mm). Note that, in FIG. 21, there is no region of negative measurement sensitivity.

Figure 22:
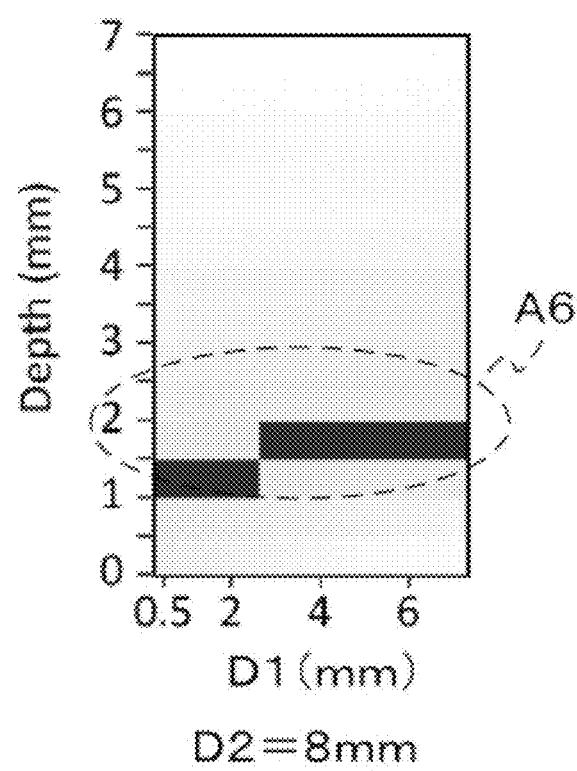
FIG. 22 is a drawing illustrating results of a simulation of measurement sensitivity per measurement depth in a case in which the object of measurement is gastrointestinal tissue and the second distance D2 is 8 mm.

FIG. 22 illustrates results of simulating the measurement sensitivity per measurement depth under conditions that are similar to those of FIG. 21, except that the second distance D2 is 8 mm and the first distance D1 is variable within the range of 0 (mm)<D1<8 (mm).

As illustrated in FIG. 22, of region A6 that is circled by the dashed line, the regions where the color is dark are the peak measurement sensitivity. As illustrated in FIG. 22, it can be understood that the measurement sensitivity is peak in the range in which the measurement depth is greater than or equal to 1.0 (mm) and less than or equal to 2.0 (mm). Note that, in FIG. 22, there is no region of negative measurement sensitivity.

Figure 23:
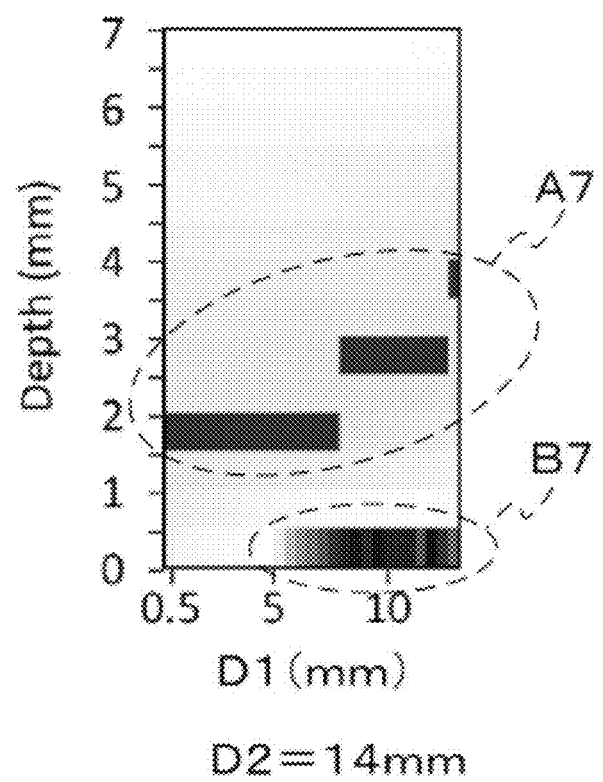
FIG. 23 is a drawing illustrating results of a simulation of measurement sensitivity per measurement depth in a case in which the object of measurement is gastrointestinal tissue and the second distance D2 is 14 mm.

FIG. 23 illustrates results of simulating the measurement sensitivity per measurement depth under conditions that are similar to those of FIG. 21, except that the second distance D2 is 14 mm and the first distance D1 is variable within the range of 0 (mm)<D1<14 (mm).

As illustrated in FIG. 23, of region A7 that is circled by the dashed line, the regions where the color is dark are the peak measurement sensitivity. As illustrated in FIG. 23, it can be understood that the measurement sensitivity is peak in the range in which the measurement depth is greater than or equal to 2.5 (mm) and less than or equal to 4.0 (mm).

Note that, in FIG. 23, the measurement sensitivity is negative in region B7 that is circled by the dashed line.

Figure 24:
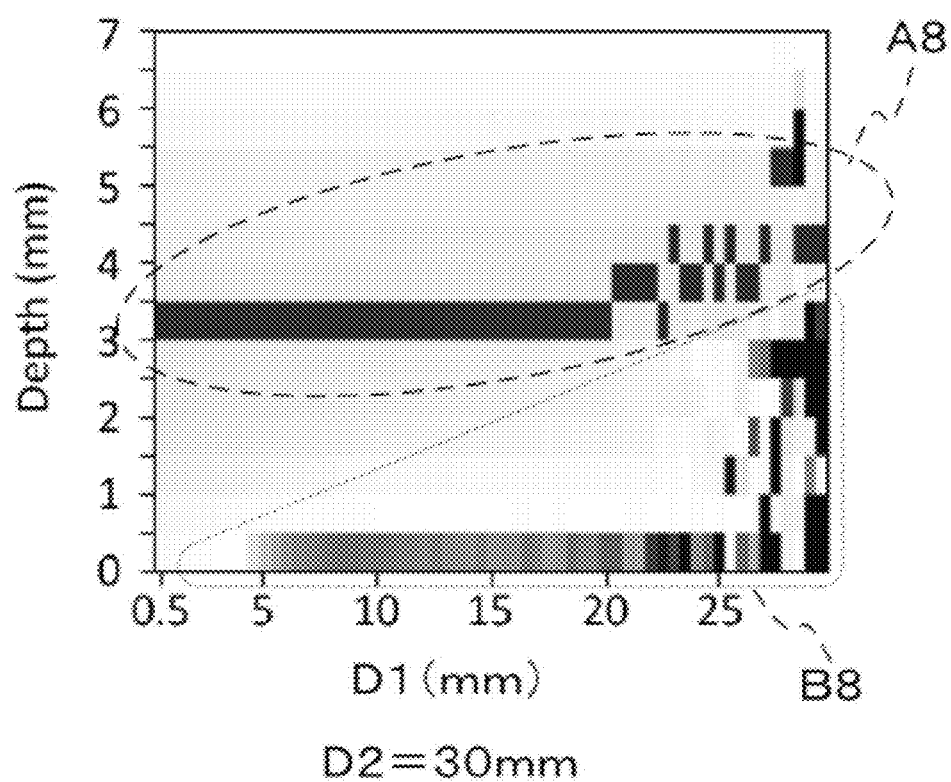
FIG. 24 is a drawing illustrating results of a simulation of measurement sensitivity per measurement depth in a case in which the object of measurement is gastrointestinal tissue and the second distance D2 is 30 mm.

FIG. 24 illustrates results of simulating the measurement sensitivity per measurement depth under conditions that are similar to those of FIG. 21, except that the second distance D2 is 30 mm and the first distance D1 is variable within the range of 0 (mm)<D1<30 (mm).

As illustrated in FIG. 24, of region A8 that is circled by the dashed line, the regions where the color is dark are the peak measurement sensitivity. As illustrated in FIG. 24, it can be understood that the measurement sensitivity is peak in the range in which the measurement depth is greater than or equal to 3.0 (mm) and less than or equal to 5.5 (mm).

Note that, in FIG. 24, the measurement sensitivity is negative in region B8 that is circled by the dashed line.

The present inventors carried out simulations similar to those of FIGS. 21~24 also for various second distances D2 other than the second distances D2 shown in FIGS. 21~24. Then, from the results of simulation shown in FIGS. 21~24 and the results of simulation other than FIGS. 21~24, the present inventors understood that, as compared with a case in which the object of measurement is skin tissue, if the first distance D1 and the second distance D2 are the same, the measurement depth at which the measurement sensitivity becomes peak is slightly more shallow.

Further, as the result of carrying out regression analysis, it was understood that the relationship among the measurement depth Dp2, the first distance D1 and the second distance D2 is expressed by the following formula.

$$Dp2=0.041\times D1+0.073\times D2+0.76 \quad (5)$$

From the above-described results of simulation, it was understood that, in a case in which the second distance D2 is less than or equal to 10 mm, the difference between measurement depth Dp1 of skin tissue and Dp2 of gastrointestinal tissue is in the range of greater than or equal to 10% and less than or equal to 20%, and that measurement sensitivity distributions of the two tissues can be calculated by the same measurement sensitivity calculation device.

Further, it was understood that, by appropriately selecting the first distance D1 and the second distance D2 in accordance with the depth of the object of measurement and the type of the tissue, the measurement depth can be changed within the range of 1~5 mm.

Note that the present embodiments do not limit the inventions relating to the claims, and further, it is not the case that all of the combinations of the features described in the description of the embodiments are essential to the means for solving the problem of the present invention. Inventions of various stages are included in the above-described embodiments, and various inventions can be extracted by combining plural constituent elements that are disclosed. Even if some of the constituent elements are eliminated from all of the constituent elements illustrated in the embodiments, structures from which several constituent elements are eliminated can be extracted as the invention provided that the results of the present invention are obtained thereby.

Further, although the above embodiments describe a case in which the measurement sensitivity calculation program 55A is installed in advance in the storage 55, the present disclosure is not limited to this. For example, the measurement sensitivity calculation program 55A may be in a form of being provided by being stored on a storage medium such as a CD-ROM (Compact Disc Read Only Memory) or the like, or may be in a form of being provided through a network.

Moreover, although the above embodiments describe a case in which the measurement sensitivity calculation processing is realized by executing a program by software structures by using a computer, the present disclosure is not limited to this. For example, the measurement sensitivity calculation processing may be a form that is realized by hardware structures or a combination of hardware structures and software structures.

Further, the flow of the processings of the measurement sensitivity calculation program described in the above-described embodiments (see FIG. 5) is an example, and it goes without saying that unnecessary steps may be deleted therefrom, new steps may be added thereto, or the order of processings may be rearranged, within a scope that does not depart from the gist of the present disclosure.

Note that the disclosure of Japanese Patent Application No. 2020-161401 is, in its entirety, incorporated by reference into the present specification. Further, all publications, patent applications, and technical standards mentioned in the present specification are incorporated by reference into the present specification to the same extent as if such individual publication, patent application, or technical standard was specifically and individually indicated to be incorporated by reference.

EXPLANATION OF REFERENCE NUMERALS

10 optical measurement device
12 probe
14 driving device
16 control section
24 light emitter
26 light receiver
33 selecting circuit
40 light emitter for ToF
42 light receiver for ToF
50 measurement sensitivity calculation device
51 controller
55 storage
55A measurement sensitivity calculation program
55B object of measurement model data
55C object of measurement depth information
60 calculating section
61 outputting section
D1 first distance
D2 second distance
M object of measurement model

The invention claimed is:

1. A measurement sensitivity calculation device comprising:
a calculating section that, in an object of measurement model that expresses an object of measurement, calculates measurement sensitivity per depth of the object of measurement by using, as the measurement sensitivity, an optical path length difference between a first optical path length expressing a length of a first optical path that is up to where light, which is emitted from a light emitter onto the object of measurement, is received at a first light receiver that is apart from the light emitter by a first distance, and a second optical path length expressing a length of a second optical path that is up to where light, which is emitted from the light emitter, is received at a second light receiver that is apart from the light emitter by a second distance; and
an outputting section that outputs the calculated measurement sensitivity per depth of the object of measurement, wherein:
the object of measurement model is a model expressing the object of measurement by a plurality of voxels, and the calculating section calculates the measurement sensitivity per depth of the object of measurement by, for each of the plurality of voxels, calculating the first optical path length and the second optical path length and calculating the measurement sensitivity, and integrating the measurement sensitivities calculated for the respective voxels per depth of the object of measurement.

2. The measurement sensitivity calculation device of claim 1, wherein the calculating section selects a plurality of groups of two light receivers that are combinations in which at least one of the first distance and the second distance is different, and calculates the measurement sensitivity per depth of the measurement object for the plurality of groups of light receivers that are selected.

3. The measurement sensitivity calculation device of claim 2, wherein the outputting section outputs the first distance and the second distance of a group of light receivers at which a depth of the object of measurement is included in a range of depths corresponding to a measurement sensitivity that is greater than or equal to a predetermined threshold value, among the plurality of groups of light receivers.

4. A measurement sensitivity calculation method comprising:
a step of, in an object of measurement model that expresses an object of measurement, calculating measurement sensitivity per depth of the object of measurement by using, as the measurement sensitivity, an optical path length difference between a first optical path length expressing a length of an optical path that is up to where light, which is emitted from a light emitter onto the object of measurement, is received at a first light receiver that is apart from the light emitter by a first distance, and a second optical path length expressing a length of an optical path that is up to where light, which is emitted from the light emitter, is received at a second light receiver that is apart from the light emitter by a second distance; and
a step of outputting the calculated measurement sensitivity per depth of the object of measurement, wherein:
the object of measurement model is a model expressing the object of measurement by a plurality of voxels, and the calculating section calculates the measurement sensitivity per depth of the object of measurement by, for each of the plurality of voxels, calculating the first optical path length and the second optical path length and calculating the measurement sensitivity, and integrating the measurement sensitivities calculated for the respective voxels per depth of the object of measurement.

5. A non-transitory recording medium storing a measurement sensitivity calculation program that is executable by a computer to perform processing, the processing comprising:
a step of, in an object of measurement model that expresses an object of measurement, calculating measurement sensitivity per depth of the object of measurement by using, as the measurement sensitivity, an optical path length difference between a first optical path length expressing a length of a first optical path that is up to where light, which is emitted from a light emitter onto the object of measurement, is received at a first light receiver that is apart from the light emitter by a first distance, and a second optical path length expressing a length of a second optical path that is up to where light, which is emitted from the light emitter, is received at a second light receiver that is apart from the light emitter by a second distance; and
a step of outputting the calculated measurement sensitivity per depth of the object of measurement, wherein:
the object of measurement model is a model expressing the object of measurement by a plurality of voxels, and the calculating section calculates the measurement sensitivity per depth of the object of measurement by, for each of the plurality of voxels, calculating the first optical path length and the second optical path length and calculating the measurement sensitivity, and integrating the measurement sensitivities calculated for the respective voxels per depth of the object of measurement.

6. An optical measurement device comprising:
a light emitter emitting light onto an object of measurement;
three or more light receivers whose distances from the light emitter are different;
a selecting section selecting two light receivers that are selected from the three or more light receivers; and
a computing section that calculates absorption degrees of lights on the basis of light intensities of lights received by the two light receivers, wherein, in an object of measurement model that expresses an object of measurement, and by using, as measurement sensitivity, an optical path length difference between a first optical path length expressing a length of a first optical path that is up to where light, which is emitted from the light emitter onto the object of measurement, is received at a first light receiver that is apart from the light emitter by a first distance, and a second optical path length expressing a length of a second optical path that is up to where light, which is emitted from the light emitter, is received at a second light receiver that is apart from the light emitter by a second distance, the selecting section selects a plurality of groups of two light receivers that are combinations in which at least one of the first distance and the second distance is different, and selects two light receivers corresponding to the object of measurement on the basis of calculation results of calculating the measurement sensitivity per depth of the object of measurement for the plurality of groups of light receivers that were selected.

7. The optical measurement device of claim 6, wherein, in a case in which the object of measurement is skin tissue, and a depth of the object of measurement is greater than or equal to 1 mm and less than or equal to 3 mm, the selecting section selects the second light receiver at which the second distance is less than or equal to 14 mm.

8. The optical measurement device of claim 6, wherein, in a case in which the object of measurement is skin tissue, the selecting section selects the first light receiver and the second light receiver that correspond to the first distance and the second distance that are nearest to the first distance and the second distance that satisfy conditions that the first distance is 1/2 of the second distance and a depth of the skin tissue is 1/5 of the second distance.

9. The optical measurement device of claim 6, wherein the selecting section selects the first light receiver and the second light receiver on the basis of a relationship of correspondence among a depth of the object of measurement, the first distance and the second distance, which relationship of correspondence is derived on the basis of calculation results of calculating the measurement sensitivity per depth of the object of measurement.

* * * * *